United States Patent [19]

Grevious

[11] Patent Number: 5,324,315
[45] Date of Patent: Jun. 28, 1994

[54] CLOSED-LOOP DOWNLINK TELEMETRY AND METHOD FOR IMPLANTABLE MEDICAL DEVICE

[75] Inventor: John J. Grevious, Minneapolis, Minn.

[73] Assignee: Medtronic, Inc., Minneapolis, Minn.

[21] Appl. No.: 106,495

[22] Filed: Aug. 12, 1993

[51] Int. Cl.⁵ .......................................... A61N 1/362
[52] U.S. Cl. .................................. 607/60; 607/32; 128/903
[58] Field of Search ....................... 607/32, 60; 128/903

[56] References Cited

U.S. PATENT DOCUMENTS

| | | |
|---|---|---|
| 3,311,111 | 3/1967 | Bowers . |
| 3,426,748 | 2/1969 | Bowers ............................... 607/28 |
| 3,518,997 | 7/1970 | Sessions . |
| 3,623,486 | 11/1971 | Berkovits . |
| 3,631,860 | 1/1972 | Lopin . |
| 3,738,369 | 6/1973 | Adams . |
| 3,805,796 | 4/1974 | Terry, Jr. . |
| 3,953,848 | 4/1976 | Dillman et al. ....................... 128/903 |
| 4,066,086 | 1/1978 | Alferness . |
| 4,208,008 | 6/1980 | Smith . |
| 4,211,235 | 6/1980 | Keller, Jr. . |
| 4,220,156 | 9/1980 | Schulman et al. ................... 128/903 |
| 4,233,985 | 11/1980 | Hartlaub . |
| 4,236,524 | 12/1980 | Powell . |
| 4,250,884 | 2/1981 | Hartlaub . |
| 4,253,466 | 3/1981 | Hartlaub . |
| 4,273,132 | 6/1981 | Hartlaub . |
| 4,361,153 | 11/1982 | Slocum et al. ....................... 607/32 |
| 4,374,382 | 2/1983 | Markowitz . |
| 4,401,120 | 8/1983 | Hartlaub . |
| 4,528,987 | 6/1985 | Slocum ............................... 607/32 |
| 4,531,523 | 7/1985 | Anderson . |
| 4,531,526 | 6/1985 | Genest ............................... 128/903 |
| 4,539,992 | 9/1985 | Calfee . |
| 4,542,532 | 9/1985 | McQuilkin . |
| 4,550,732 | 11/1985 | Batty, Jr. . |
| 4,556,063 | 12/1985 | Thompson . |
| 4,562,840 | 1/1986 | Batina et al. ........................ 607/32 |
| 4,571,589 | 2/1986 | Slocum . |
| 4,676,248 | 6/1987 | Berntson . |
| 4,987,897 | 1/1991 | Funke ................................. 607/32 |
| 5,052,388 | 10/1991 | Sivula . |
| 5,117,825 | 6/1982 | Grevious ............................ 607/32 |
| 5,127,404 | 7/1992 | Wyborny . |
| 5,168,871 | 12/1992 | Grevious ............................ 128/903 |
| 5,226,413 | 7/1993 | Bennett . |

OTHER PUBLICATIONS

Donaldson, D. den. "Medical & Biological Engineering & Computing" vol. 23, No. 3, May, 1985, p. 291.

*Primary Examiner*—William E. Kamm
*Attorney, Agent, or Firm*—Reed A. Duthler; Harold R. Patton

[57] ABSTRACT

A closed loop system for attaining premium telemetry performance for vector field electromagnetically coupled telemetry systems. The disclosed system utilizes a linear ramped envelope for downlink RF bursts, resulting in a detected pulse width in the implanted device which is proportional to the downlink detection margin. The detected pulse width, when uplink telemetered to an external programming unit allows the programming unit to generate a telemetry status feedback signal for the user positioning the programming head with respect to the implant site. Feedback based upon both uplink and downlink signal strength in especially advantageous in dual-coil systems where there are distinct and unique coupling coefficients for uplink and downlink.

12 Claims, 5 Drawing Sheets

CLOSED-LOOP DOWNLINK TELEMETRY AND METHOD FOR IMPLANTABLE MEDICAL DEVICE

FIELD OF THE INVENTION

This invention relates to the field of implantable medical devices, and more particularly relates to implantable medical devices which include a telemetry subsystem.

BACKGROUND OF THE INVENTION

Since the introduction of the first implantable pacemakers in the 1960's, there have been considerable advancements both in the field of electronics and the field of medicine, such that there is presently a wide assortment of commercially-available implantable medical devices. The class of implantable medical devices now includes not only pacemakers, but also implantable cardioverters, defibrillators, neural stimulators, and drug administering devices. Today's state-of-the-art implantable medical devices are vastly more sophisticated and complex than early pacemakers, capable of performing significantly more complex tasks. The therapeutic benefits of such devices have been well-proven.

As the functional sophistication and complexity of implantable medical devices has increased over the years, it has become increasingly more important for such devices to be equipped with a telemetry system for enabling them to communicate with an external unit.

For example, shortly after the introduction of the earliest fixed-rate, non-inhibited pacemakers, it became apparent that it would be desirable for a physician to non-invasively exercise at least some amount of control over the device, e.g., to turn the device on or off or adjust the fixed pacing rate, after implant. In early devices, one way the physician was able to have some control over implantable device operation was through the provision of a magnetic reed switch in the implantable device. After implant, the reed switch would be actuated by placing a magnet over the implant site. Reed switch closure could then be used, for example, to alternately activate or deactivate the device. Alternatively, the fixed pacing rate of the device could be adjusted up or down by incremental amounts based upon the duration of reed switch closure. Many different schemes utilizing a reed switch to adjust parameters of implanted medical devices have been developed. See, for example, U.S. Pat. No. 3,311,111 to Bowers, U.S. Pat. No. 3,518,997 to Sessions, U.S. Pat. No. 3,623,486 to Berkovits, U.S. Pat. No. 3,631,860 to Lopin, U.S. Pat. No. 3,738,369 to Adams et al., U.S. Pat. No. 3,805,796 to Terry, Jr., and U.S. Pat. No. 4,066,086 to Alferness et al.

As new, more advanced features are incorporated into implantable devices, it is typically necessary to convey correspondingly more information to the device relating to the selection and control of those features. For example, if a pacemaker is selectively operable in various pacing modes (e.g., VVI, VDD, DDD, etc . . . ), it is desirable that the physician or clinician be able to non-invasively select a mode of operation. Similarly, if the pacemaker is capable of pacing at various rates, or of delivering stimulating pulses of varying energy levels, it is desirable that the physician or clinician be able to select, on a patient-by-patient basis, appropriate values for such variable operational parameters.

Even greater demands are placed upon the telemetry system in implantable devices having such advanced features as rate adaptation based upon activity sensing, as disclosed, for example, in U.S. Pat. No. 5,052,388 to Sivula et al. entitled "Method and Apparatus for Implementing Activity Sensing in a Pulse Generator", in U.S. Pat. No. 5,266,413 issued to Bennett et al, entitled "Rate Responsive Pacemaker and Method for Automatically Initializing the Same", and in U.S. patent application Ser. No. 07/880,877, filed May 11, 1992 in the name of Shelton et al., entitled "Work-Modulated Pacing Rate Deceleration". The Sivula et al. '388 patent, the Bennett et al '413 patent and the Shelton et al. '877 application are each hereby incorporated by reference herein in their entireties.

The information which is typically communicated to the implantable device in today's state-of-the-art pacemakers includes: pacing mode, multiple rate response settings, electrode polarity, maximum and minimum pacing rates, output energy (output pulse width and/or output current), sense amplifier sensitivity, refractory periods, calibration information, rate response attack (acceleration) and decay (deceleration), onset detection criteria, and perhaps many other parameter settings.

The need to be able to communicate more and more information to implanted devices quickly rendered the simple reed-switch closure arrangement insufficient. Also, it has become apparent that it would also be desirable not only to allow information to be communicated to the implanted device, but also to enable the implanted device to communicate information to the outside world.

For diagnostic purposes, for example, it is desirable for the implanted device to be able to communicate information regarding its operational status to the physician or clinician. State of the art implantable devices are available which can even transmit a digitized ECG signal for display, storage, and/or analysis by an external device.

As used herein, the terms "uplink" and "uplink telemetry" will be used to denote the communications channel for conveying information from the implanted device to an external unit of some sort. Conversely, the terms "downlink" and "downlink telemetry" will be used to denote the communications channel for conveying information from an external unit to the implanted device.

Various telemetry systems for providing the necessary communications channels between an external unit and an implanted device have been shown in the art. Telemetry systems are disclosed, for example, in the following U.S Pats: U.S. Pat. No. 4,539,992 to Calfee et al. entitled "Method and Apparatus for Communicating With Implanted Body Function Stimulator"; U.S. Pat. No. 4,550,732 to Batty, Jr. et al. entitled "System and Process for Enabling a Predefined Function Within An Implanted Device"; U.S. Pat. No. 4,571.589 to Slocum et al. entitled "Biomedical Implant With High Speed, Low Power Two-Way Telemetry"; U.S. Pat. No. 4,676,248 to Berntson entitled "Circuit for Controlling a Receiver in an Implanted Device"; U.S. Pat. No. 5,127,404 to Wyborny et al. entitled "Telemetry Format for Implanted Medical Device"; U.S. Pat. No. 4,211,235 to Keller, Jr. et al. entitled "Programmer for Implanted Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above-referenced patents are employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled Programmable Digital Cardiac Pacemaker with Means to Override Effects of Reed Switch Closure"; U.S. Pat. No. 4,233,985 entitled "Multi-Mode Programmable Digital Cardiac Pacemaker"; U.S. Pat. No. 4,253,466 entitled "Temporary and Permanent Programmable Digital Cardiac Pacemaker"; and U.S. Pat. No. 4,401,120 entitled "Digital Cardiac Pacemaker with Program Acceptance Indicator".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modelled as an air-core coupled transformer. Examples of such a telemetry system are shown in the above-referenced Thompson et al. '063 and Hartlaub et al. '120 patents.

In order to communicate digital data using RF telemetry, a digital encoding scheme such as is described in U.S. Pat. No. 5,127,404 to Wyborny et al. entitled "Improved Telemetry Format" is used. In particular, for downlink telemetry a pulse interval modulation scheme may be employed, wherein the external programmer transmits a series of short RF "bursts" or pulses in which the during of an internal between successive pulses (e.g., the interval from the trailing edge of one pulse to the trailing edge of the next) encodes the data. In particular, a shorter interval encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data. The Wyborny et al. '404 patent is hereby incorporated by reference herein in its entirety.

Programming units such as the above-described Hartlaub et al. Programmer typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

For programming arrangements such as the one just described, both uplink and downlink telemetry signal strength vary as a function of programming head positioning. Thus, it is important for the programming head to be properly positioned over the patient's implant site, not only so that the magnet in the programming head is close enough to the implanted device to cause reed switch closure, but also so that the downlink RF signals can be detected in the implanted device and the uplink signals can be detected by the programming head. If the programming head is too far away from the implanted device, the attenuation of RF signals transmitted across the boundary of the patient's skin may be too great, preventing the telemetry link from being established.

Although both uplink and downlink signal strength vary as a function of head position, the coupling maps for uplink and downlink telemetry may be different. That is, what may be optimal positioning for uplink telemetry may be less optimal for downlink telemetry, and vice versa.

Differences between the uplink and downlink telemetry coupling maps arise when a so-called "dual-coil" system is employed in the programmer. An example of a dual-coil telemetry system is described in U.S. Pat. No. 4,542,532 to McQuilkin, entitled "Dual Antenna Receiver". The McQuilkin '532 patent is hereby incorporated by reference herein in its entirety. In a dual-coil system, two coils are connected in series opposition to achieve noise cancellation in the receive mode. The two coil series-opposing configuration makes the programmer sensitive to the curl of magnetic fields. Such curl sensitivity results in a significant increase in noise rejection over a single-coil antenna for in-band, spatially-aligned interference fields present in the proximity of the antenna.

For transmission from a dual-coil antenna, the two coils are configured in "parallel aiding" fashion, such that the magnetic field transmitted by the antenna is effectively doubled.

Often, medical device programmers, for example the Model 9710 or 9760 programmers commercially available from Medtronic, Inc., are provided with a Head Positioning Indicator, either audible or visible, for indicating to the physician or clinician when the programming head is properly located over a patient's implanted device. In the prior art, the technique most commonly used for determining when the programming head is properly positioned can be characterized generally as "open loop", in that the determination of correct head positioning is based solely upon an assessment of whether the uplink signal (i.e., the signal transmitted from the implanted device to the external programming head) meets some minimum requirement. In particular, uplink signal strength is measured based upon the operating gain of the uplink telemetry receiver. In such open loop verification systems, adequate downlink signal strength is not tested.

An example of an open loop system for determining the proper positioning of a programming head is described in U.S. Pat. No. 4,531,523 to Anderson, entitled "Digital Gain Control for the Reception of Telemetry Signals From Implanted Medical Devices". The '523 patent relates to a system wherein verification of the programming of an implanted device is provided by the transmission of predetermined signals from the implanted device. When errors are detected in these uplink signals, the number of errors are counted over a period of time. If more than a predetermined number of errors occur in that time, the gain of the programming unit receiver is adjusted downward by a predetermined amount. This adjustment continues until uplink signals are received without error. As an open loop system, however, the system of the '523 patent does not test for errors in downlink telemetry signals, and does not evaluate the strength of the received downlink telemetry signals.

When downlink signal strength cannot be tested, it is important for the physician or clinician to be able to otherwise verify that programming signals transmitted from the programming head are accurately received and processed by the implanted device. To this end, a system is described in the above-referenced Hartlaub et al. '120 patent wherein circuitry in the implanted device performs several different checks on the detected downlink programming signal, including a parity check and an access code check, and issues a program acceptance signal if the downlink programming is found to be valid.

As those of ordinary skill in the art will appreciate, a communications protocol using handshaking can verify that a minimum downlink field strength for detection in the implanted device exists prior to signalling the physician or clinician that correct head positioning has been achieved. However, a handshaking protocol cannot provide any information useful for optimization of head positioning to ensure an adequate operating margin. This means that proper programming head positioning may be indicated even though the programming head is actually marginally positioned, such that a very slight shift in positioning (e.g., due to patient motion) results in downlink telemetry failure.

Those of ordinary skill in the art will appreciate that one possible way to ensure an adequate margin between the strength of detected downlink signals in an implanted medical device and the device's detection threshold would be to transmit downlink telemetry signals having much larger than nominal amplitudes. From an energy consumption standpoint, this solution is particularly feasible when used in the context of a line-powered (as opposed to battery-powered) external programming unit, since for a line-powered programming unit, energy consumption is not a critical factor. If extremely strong downlink signals were transmitted, the programmer could be assured that the signals will be strong enough to be detected by the implanted device. In this way, the need for a downlink signal strength indication would be obviated.

There are several disadvantages, however, with the use of excessively strong downlink telemetry signals to ensure their detection by the implanted device. First, while power consumption is not a crucial factor in line-powered programmers, it is becoming increasingly common for programming units to be portable and battery-powered, so that they may be easily transported and used in a variety of clinical and/or non-clinical settings. For battery-powered programmers, it would be inefficient and undesirable to consume the limited battery power with unnecessarily high-level downlink signals.

Perhaps a more critical disadvantage of transmitting high-level downlink signals is the possibility that the large RF energy bursts in the downlink transmission may interfere with the operation of the implanted device. In particular, for very high-energy downlink telemetry pulses, it is possible for the downlink signal to induce voltages on implanted pace/sense leads. Such induced voltages may be interpreted by the implanted device's sensitive sensing circuitry (e.g., pacemaker) as cardiac events and may thereby cause pacemaker inhibition or lead to loss of synchronization with intrinsic cardiac activity. This problem is likely to worsen as improved (i.e., more sensitive) sensing circuitry is developed. It is also possible that when downlink telemetry is performed continuously for long periods of time (e.g., during clinical diagnostic tests on the patient), that excessively large downlink signals could cause thermal complications, i.e., cause the implanted device to exhibit an undesirable increase in temperature.

In the prior art, implanted devices have been provided with clamping diodes to prevent overdriving of the implanted devices' telemetry inputs and circuitry to dissipate energy induced in the implanted downlink telemetry receiver coil. For example, energy induced in a device's receiver coil can to a limited extent be redirected to the device's battery.

Nonetheless, problems with excessive energy from downlink telemetry are likely to be exacerbated in state-of-the-art and future devices to which more and more information must be communicated over relatively long periods of time.

A further problem arising from the inability, in prior art programming arrangements to ascertain the strength of the downlink signal as detected by the implanted device is that telemetry failures are difficult to troubleshoot. This is due, in part, to the fact that when downlink signals are not successfully received, the programmer cannot tell whether the problem lies in the positioning of the programming head, in inadequate downlink signal strength, or elsewhere.

The use of a secondary (feedback) sensing coil within the programmer itself to sample the downlink signal intensity within the programming head compensates for such variables as supply voltage variation, temperature-induced variation, parts tolerance variation, transmit antenna detuning and transmit antenna loading. However, a sensing coil does not compensate for field distortions beyond the programming head that do not result in intensity changes in the feedback sensing coil. The field is merely standardized and does not dynamically adjust to compensate for field distortion or attenuation that occurs in and around the implanted device itself, nor for the alignment of the electromagnetic field vector with the implanted device's downlink sensing vector.

As a result of the foregoing considerations, it is believed that it would be desirable to provide a programmer with the capability of evaluating the strength of downlink telemetry signals as detected by the implanted device, i.e., to enable the implanted device to communicate to the programmer information about the strength of downlink signals after they have crossed the implant boundary. Such capability would be particularly desirable in the context of dual-coil systems, wherein the uplink and downlink coupling maps are different due to the different coil configurations used in the programmer for transmission and reception. With such a capability, the programmer could dynamically adjust the amplitude of downlink telemetry pulses, such that downlink signals would be transmitted at a level known to exceed the implanted device's detection threshold. At the same time, the programmer would minimize transmission of excessively or unnecessarily large downlink signals which could lead to the aforementioned problems with telemetry receiver overdriving, pacemaker inhibition due to induced voltages applied to the sensing circuitry, and the like.

If the received downlink can be controlled, programmers with very high output level capabilities could be used to extend the range of the system.

SUMMARY OF THE INVENTION

In accordance with the present invention, therefore, there is provided a telemetry system in which the implanted device can communicate to the external device information regarding the detected downlink signal strength, and in which the external programmer can control the amplitude of downlink signals to ensure an adequate margin above the implanted device's detection threshold while at the same time avoiding unnecessarily high-level downlink transmission.

In accordance with one feature of the present invention, a specific type of downlink telemetry pulse is transmitted from the external programmer to the implanted device. In particular, such downlink pulses are RF bursts having a linear ramping envelope. The morphologic characteristics of the downlink burst envelope are such that the amplitude of the signal as detected by the implanted device's receiver, relative to the receiver's detection threshold, can be ascertained by measuring the time that the detected burst exceeds the receiver's threshold. This information can be communicated in digital form to the external programming unit.

In accordance with another aspect of the present invention, the external programming unit can modulate the peak amplitude of downlink burst envelopes based upon the information provided from the implanted device regarding the relative strength of detected downlink signals. In this way, the external programmer can ensure an adequate safety margin over the implanted device's detection threshold, while at the same time avoid transmission of unnecessarily high energy downlink signals.

In accordance with still another aspect of the present invention, the external programming unit can provide a telemetry status indication to the physician or clinician which is based not only upon uplink signal strength but also upon downlink signal strength. In this way, device programming is conducted more efficiently and reliably than in the prior art. In addition, the power consumption of the external device is minimized, rendering the present invention particularly well-suited to incorporation into portable, battery-powered programming units.

A further advantage of the present invention is that, given information regarding the strength of downlink signals as actually detected by the implanted device, during design and performance verification and quality assurance assessment, the downlink signal strength data can be used to produce a mapping of the downlink signal. Moreover, each implantable device's downlink sensitivity geometry can be independently examined prior to being packaged and sold.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
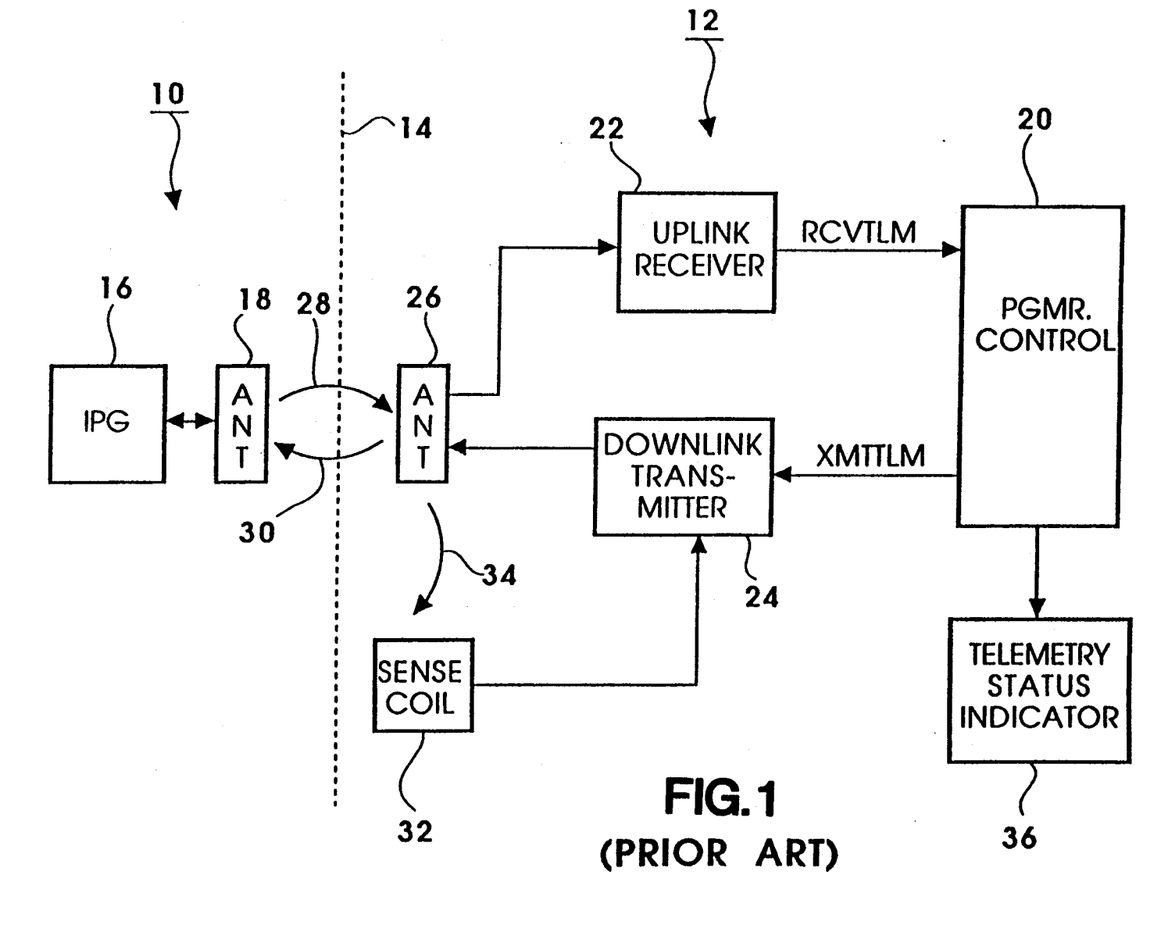
FIG. 1 is a block diagram of a prior art pacemaker and programming unit combination including an uplink-/downlink telemetry system.

Referring to FIG. 1, there is shown a block diagram of a prior art medical device system including an implantable device designated generally as 10 and an external programming unit designated generally as 12. A dashed line 14 in FIG. 1 represents the boundary (i.e., the patient's skin) between implanted device 10 and external device 12. It is believed that the present invention may be advantageously and beneficially practiced in conjunction with various different types of implanted devices which are capable of being non-invasively programmed by means of an external programming/control unit. Those of ordinary skill in the art will appreciate that implanted device 10 may be, for example, a cardiac pacemaker, cardioverter, defibrillator, neural stimulator, drug administering device, or the like, and it is believed that those having the benefit of the present disclosure will be readily able to adapt the present invention for use with these or other types of implanted devices.

As shown in FIG. 1, implanted device 10 includes, in the illustrative embodiment, an implantable pulse generator (IPG) system 16 in communication with an antenna 18. Antenna 18 may be of the "dual-coil" type, as previously described, and as described in the above-referenced McQuilkin '532 patent.

IPG system 16 may be, for example, substantially the same as the pacemaker described in the above-reference Sivula et al. '388 patent. As such, IPG system 16 includes a telemetry subsystem for receiving and storing downlink programming and control signals detected by antenna 18, and for issuing various uplink signals to antenna 18 for transmission to external unit 12. The telemetry subsystem of IPG 16 may correspond, for example, to those disclosed in U.S. patent application Ser. No. 08/085,489, entitled "Pacemaker Telemetry System", filed Jun. 28, 1993 by Ryan et al., (which application is hereby incorporated by reference herein in its entirety) and/or the above-referenced Wyborny et al. '404 and Thompson '063 patents.

Antenna 18 is preferably implemented as a multi-turn wire coil housed within the implanted device's hermetic encapsulation, in accordance with common practice in the art.

On the external side of boundary 14, external programming unit 12 is preferably implemented as a microprocessor-based system, as in the case of the Model 9710, 9765, or 9790 programming units manufactured and commercially available from Medtronic, Inc., Minneapolis, Minn. External programming unit 12 includes programmer control circuitry coupled to telemetry subsystem comprising an uplink telemetry receiver 22 and a downlink telemetry transmitter 24 coupled to an antenna 26. Those of ordinary skill in the art will appreciate that antenna 26 is preferably disposed within a handheld programming head (not shown), in accordance with common practice in the art, so that the antenna may be conveniently placed above a patient's implant site. When so positioned, antenna 26 receives uplink telemetry signals transmitted from implanted antenna 18, as indicated by arrow 28, and transmits downlink telemetry signals to be received by implanted antenna 18, as indicated by arrow 30.

With continued reference to FIG. 1, external unit 12 also includes a sense coil 32, also disposed in the programming head in proximity to antenna 26. Sense coil 32 is used to regulate the strength of downlink telemetry signals. In particular, sense coil 32 is adapted to receive the downlink telemetry signals transmitted from antenna 26 (as indicated by arrow 34) and to provide an indication of transmitted signal strength to transmitter 24. Those of ordinary skill in the art will appreciate that sense coil 32 thereby functions as a type of automatic gain control circuit (AGC). If the signal detected by sense coil 28 is too weak, the drive of transmitter 24 can be increased accordingly; conversely, if sense coil 28 senses that the downlink signal transmitted from antenna 26 is too strong, the drive of transmitter 24 can be reduced.

Of course, sense coil 32 is in a fixed relation with antenna 26 and is therefore capable only of sensing the initial transmission strength of downlink signals, i.e., not the strength of the signals actually detected by an implanted device's receiver. Sense coil 32 is not capable of determining the strength of downlink signals as received by implanted antenna 18 after such signals have been transmitted across implant boundary 14. Thus, even if downlink signals are determined by sense coil 32 to be sufficiently strong, improper positioning of the programming head with respect to implanted antenna 18 may nonetheless prevent the downlink signals from being received by implantable device 10.

In order to provide some feedback as to the proper positioning of external antenna 26 with respect to implanted antenna 18, prior art devices such as that shown in FIG. 1 have employed a position indicator 36, which may be, for example, an audible tone generator and/or a visible indicator such as a light-emitting diode (LED) or the like. When uplink telemetry signals are received by antenna 26 and receiver 22, the strength of the received signals can be assessed, and the accuracy of the uplink signal content can be verified, as with parity checking, error checking codes and the like embedded in the uplink signal. When uplink signal strength and accuracy are confirmed, programmer control circuit 20 will cause position indicator 36 to indicate that an uplink telemetry link has been established. If adequate signal strength and content accuracy cannot be confirmed (i.e., if the uplink telemetry link is broken), position indicator 36 will so indicate. In this event, prior art devices require that the physician or clinician move the programming head around until uplink telemetry can be re-established.

Those of ordinary skill in the art will appreciate that the above-described prior art position indicating arrangement does not take into account the fact that acceptable positioning of antenna 26 with respect to antenna 18 does not in all cases correspond to acceptable positioning of antenna 18 with respect to antenna 26 when antenna 26 is implemented with dual coils where the coils are connected series opposing for uplink reception and parallel aiding for downlink transmissions. That is, prior art position indicating arrangements do not address potential for above-described differences in the coupling maps for uplink and downlink telemetry.

Figure 2:
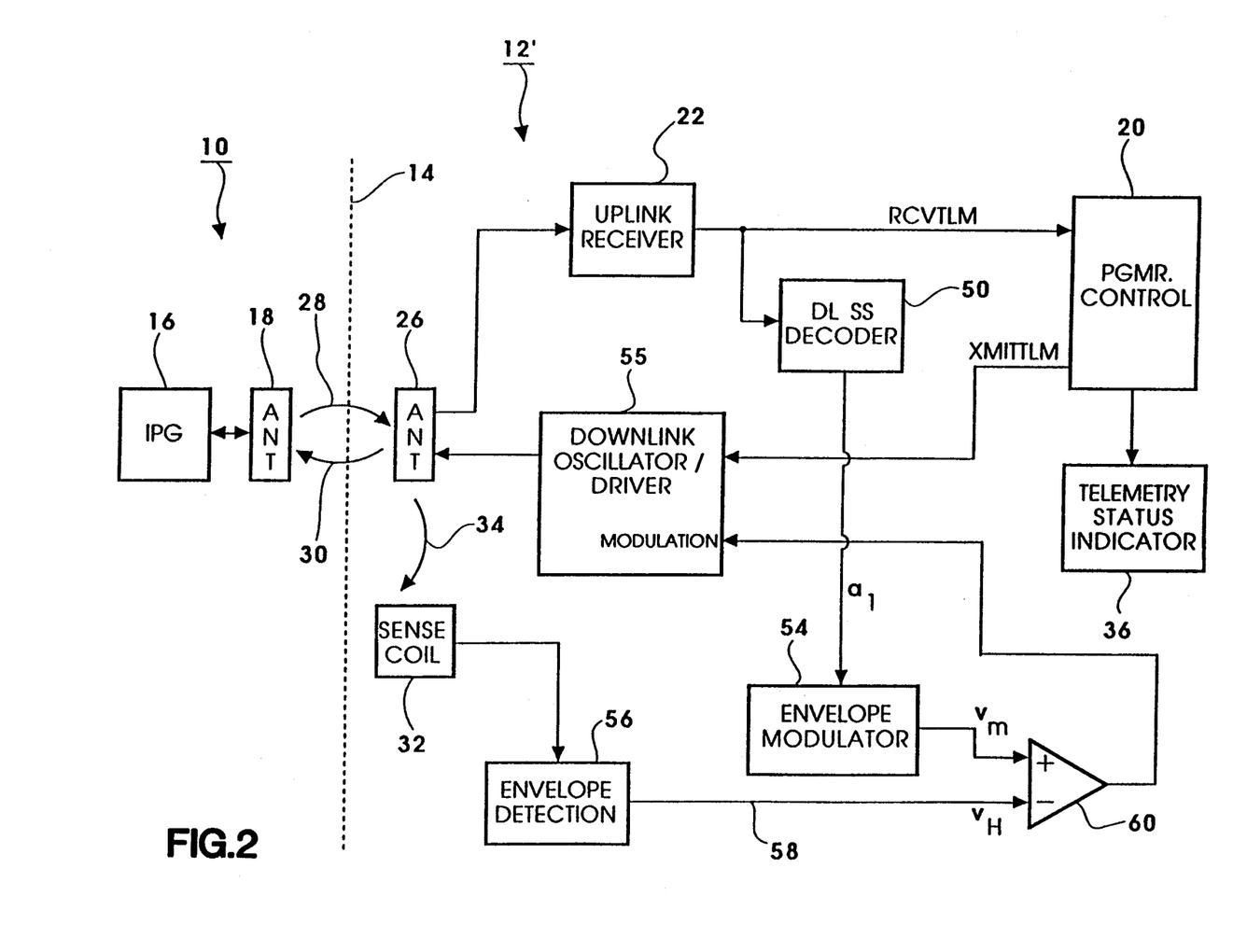
FIG. 2 is a block diagram of a pacemaker and programming unit combination employing a telemetry system in accordance with a presently preferred embodiment of the invention.

In FIG. 2, there is shown a block diagram of a implantable device system in accordance with one embodiment of the present invention, wherein provision is made for assessment of both uplink and downlink signal strength, as will be hereinafter described in greater detail. It should be noted that components of the system of FIG. 2 which are the same as those from FIG. 1 have the same reference numerals in both figures.

Figure 3:
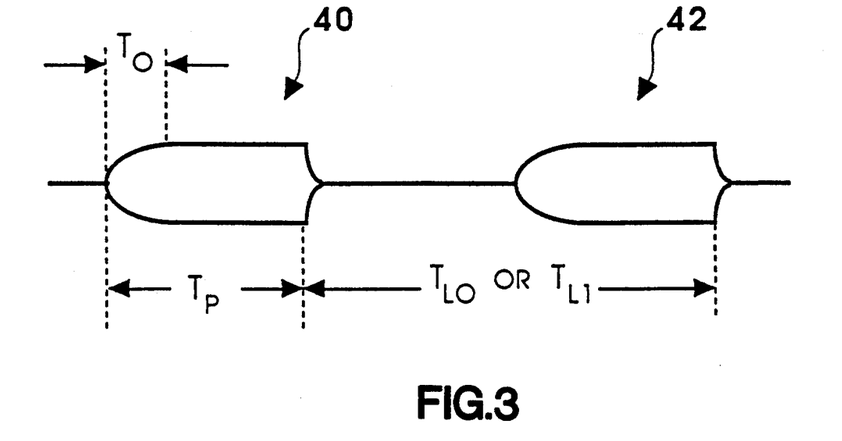
FIG. 3 is a diagram illustrating envelopes of downlink telemetry signals for a prior art telemetry protocol.

The operation of the implanted device system of FIG. 2 can perhaps be best understood and appreciated by first considering the manner in which information is communicated between an external programmer, designated as 12' in FIG. 2, and implanted device 10. In FIG. 3, there is depicted a portion of a downlink signal employed in the prior art. As previously noted, downlink telemetry has been known to be performed in the prior art using a pulse interval modulation scheme, wherein digital information (1's and 0's) is encoded into a pulse stream by modulating the trailing-edge to trailing-edge time between successive pulses. As shown in FIG. 3, each pulse in the pulse stream, for example the pulse designated as 40 in FIG. 3, lasts for a predetermined duration $T_p$, and typically has a non-linear increase in envelope amplitude on the rising edge.

It is to be understood that FIG. 3 depicts the envelope of a downlink telemetry signal; that is, pulses such as pulse 40 are actually "bursts" of a radio-frequency oscillating signal, each burst having the shape or envelope as shown. In the presently preferred embodiment of the invention, downlink pulses are burst of a 175-kHz oscillating signal. In the exemplary embodiment, each burst lasts for $T_p = 350$-$\mu$Sec, and includes an initial rising portion lasting for $T_o \leq 100$-$\mu$Sec.

As those of ordinary skill in the art will appreciate, pulse interval modulation involves varying the time between the trailing edges of two successive pulses in the downlink telemetry pulse stream. In FIG. 3, the interval between the trailing edge of pulse 40 and the trailing edge of a second pulse 42, designated "$T_{L0}$ or $T_{L1}$", represents the time interval corresponding to a binary "0" (or binary "1") encoded into the stream. A longer (or shorter) interval may then be used to encode the other binary value, binary "1" ( or binary "0").

Figure 4:
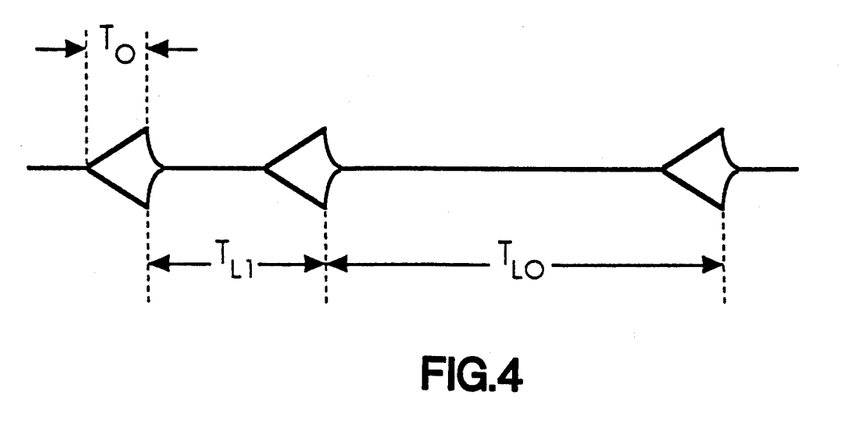
FIG. 4 is a diagram illustrating envelopes of downlink telemetry signals for a telemetry protocol in accordance with the embodiment of the invention from FIG. 2.

FIG. 4, there is shown the envelope waveform of a downlink telemetry signal in accordance with one embodiment of the present invention. The modulation scheme represented in FIG. 4 is once again trailing-edge to trailing-edge pulse interval modulation as for FIG. 3. However, the envelopes of pulses in the downlink signal of FIG. 4 include only a linear ramping portion of duration $T_o$. As shown in FIG. 4, a binary "1" is encoded as a shorter interval of duration $T_{L1}$, while a binary "0" is encoded as a longer interval of duration $T_{L0}$.

Figure 5:
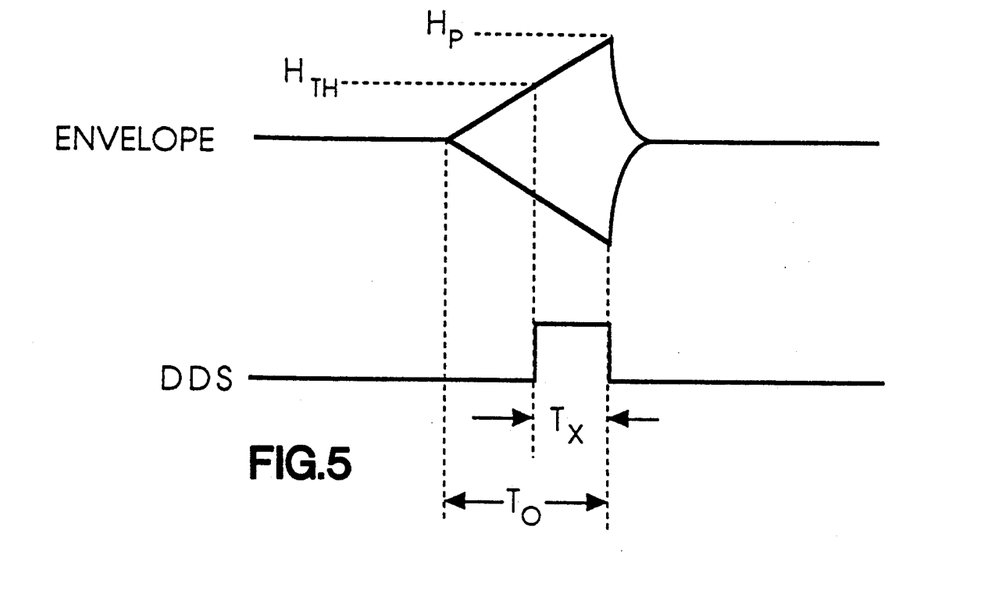
FIG. 5 is a diagram showing, in isolation, a downlink RF burst envelope from the downlink signal from FIG. 4.

Referring to FIG. 5, there is shown a single burst envelope (ENVELOPE) from the pulse stream of FIG. 4 and a detected downlink signal (DDS) representing the telemetry signal derived by the IPG telemetry system from the transmitted burst. Again, it is to be understood that the ENVELOPE of FIG. 5 depicts an envelope for a 175-kHz burst that is actually transmitted from the programmer's downlink transmitter. In FIG. 5, the dashed line $H_{TH}$ represents the magnetic field threshold of the IPG's downlink receiver circuitry; that is, magnetic fields of magnitude less than $H_{TH}$ are not received by the IPG's downlink telemetry receiver. Accordingly, in the DDS signal of FIG. 5 it can be seen that the derived downlink telemetry pulse DDS has a duration $T_x$ less than the duration $T_o$ of the ENVELOPE, since the linear ramping of the ENVELOPE is such that the receiver threshold $H_{TH}$ is not reached until some point after the start of the ENVELOPE.

Due to the linearity of upward ramping in the ENVELOPE of downlink RF bursts transmitted to implanted device 10, those of ordinary skill in the art will appreciate that for a given maximum amplitude $H_P$ of the ENVELOPE, the duration $T_x$ of the pulse in the detected downlink signal DDS is directly proportional to the margin between the IPG receiver's magnetic field threshold level $H_{TH}$ and the maximum amplitude $H_P$ of the detected ENVELOPE. In particular, the DDS pulse timing and the magnetic field strength are related according to the following equation:

$$T_x(H_{TH}, H_P) = T_O\left(1 - \frac{H_{TH}}{H_P}\right)$$

Given the foregoing relation, for an implanted downlink telemetry receiver having a known magnetic field sensitivity threshold $H_{TH}$, the maximum amplitude of detected downlink telemetry pulses can be calculated once $T_X$ is known. In particular, the maximum amplitude $H_P$ of the downlink telemetry pulse envelopes as actually seen by the implanted downlink telemetry receiver is given by the following equation:

$$H_P = H_{TH}\left(\frac{T_O}{T_O - T_x}\right)$$

Referring now to the block diagram of FIG. 2, in which a presently preferred embodiment of the invention is shown, uplink telemetry signals transmitted from antenna 18 in implanted device 10 are detected by antenna 26 in the 26 in the external programming unit and applied to uplink receiver 22, which converts the sequence of RF bursts in the uplink signal into a sequence of rectangular pulses, in accordance with conventional practice. The pulse stream RCVTLM from receiver 22 is applied to programmer control circuit 20, which decodes the uplink telemetry information. As previously noted, the presently preferred embodiment of the invention employs a pulse position modulation scheme for uplink telemetry, although it is contemplated that the particular type of uplink encoding used is not critical to the understanding or practice of the present invention, and that the present invention may be advantageously practiced in conjunction with systems using various different types of uplink encoding.

The RCVTLM square pulse stream is also applied to a downlink signal strength decoder (DS SS decoder) 50. Decoder circuit 50 operates to decode information transmitted by implanted device 10 regarding the length of the time interval $T_x$ in a previously transmitted linear ramp downlink pulse, which time interval reflects the downlink signal strength as previously described with reference described with reference to FIG. 5. Downlink signal strength decoder 50 then issues a downlink signal strength signal, hereinafter designated as signal $a_1$ on line 52, where the signal $a_1$ reflects the length of this $T_x$ interval. The $a_1$ signal on line 52 is applied to an input of an envelope modulator circuit 54 to be hereinafter described in greater detail.

With continued reference to FIG. 2, downlink signal strength is determined through the downlink transmission of a linear ramping pulse such as the one just described with reference to FIG. 5. In the system depicted in FIG. 2, the transmission of all downlink telemetry pulses is initiated by programmer control circuit 20 issuing square pulses at times when telemetry pulses are to be transmitted. The square pulses, which have a width corresponding to the specified width of downlink telemetry pulses, are conducted on the line designated as XMITTLM in FIG. 2, to be applied to the input of a downlink oscillator/driver circuit 55.

Regarding the $a_1$ signal on the line 52 from DL SS decoder circuit 50, it is contemplated that this signal may be an analog voltage whose amplitude is proportional to $T_x$. In particular, the signal $a_1$ may have an amplitude ranging from zero volts to $a_1$(MAX) volts.

As in the prior art embodiment previously described with reference to FIG. 1, the downlink telemetry signal is detected by sense coil 32 disposed in proximity to antenna 26 in the programming head. As shown in FIG. 2, the downlink signal detected by sense coil 32 is applied to an envelope detection circuit, which essentially performs a rectification of the RF pulses in the downlink signal in order to produce an output signal $v_H$ on the line 58, where $v_H$ corresponds generally to the envelope of the downlink telemetry waveform. The $v_H$ signal is applied to the negative (inverting) input of a differential amplifier 60.

Envelope modulator circuit 54, which receives the $a_1$ signal whose amplitude is proportional to the $T_X$ interval of a linear ramping downlink signal previously detected by implantable device 10, produces an output signal $v_m$ which is applied to the positive (non-inverting) input of differential amplifier 60. Differential amplifier thus produces an output signal $v_c$, which is an analog voltage derived as a function of the signals $v_m$ and $v_H$. In particular, the modulation signal $v_c$ represents a feedback signal to ensure that the envelope of the signal detected by sense coil 32 has the amplitude specified by DL SS decoder 50. That is, differential amplifier 60 compares the signal $v_m$ from envelope modulator 54, representing the desired envelope for downlink bursts, and the $v_H$ signal from envelope detection circuit 56, representing the actual envelope for downlink bursts. When this comparison indicates that the actual downlink bursts do not have the desired amplitude, this will be reflected in the modulating signal $v_c$. The exact waveform of modulating signal $v_c$ is a function of other parameters in the transmitter loop such as the oscillator/driver forward gain factor. The modulating signal $v_c$ is applied to the MODULATION input of downlink oscillator/driver circuit 55. Oscillator/driver circuit 55, in turn, generates ramped downlink RF bursts having peak amplitudes which reflect the amplitude of the modulating signal applied to its MODULATION input.

Figure 6:
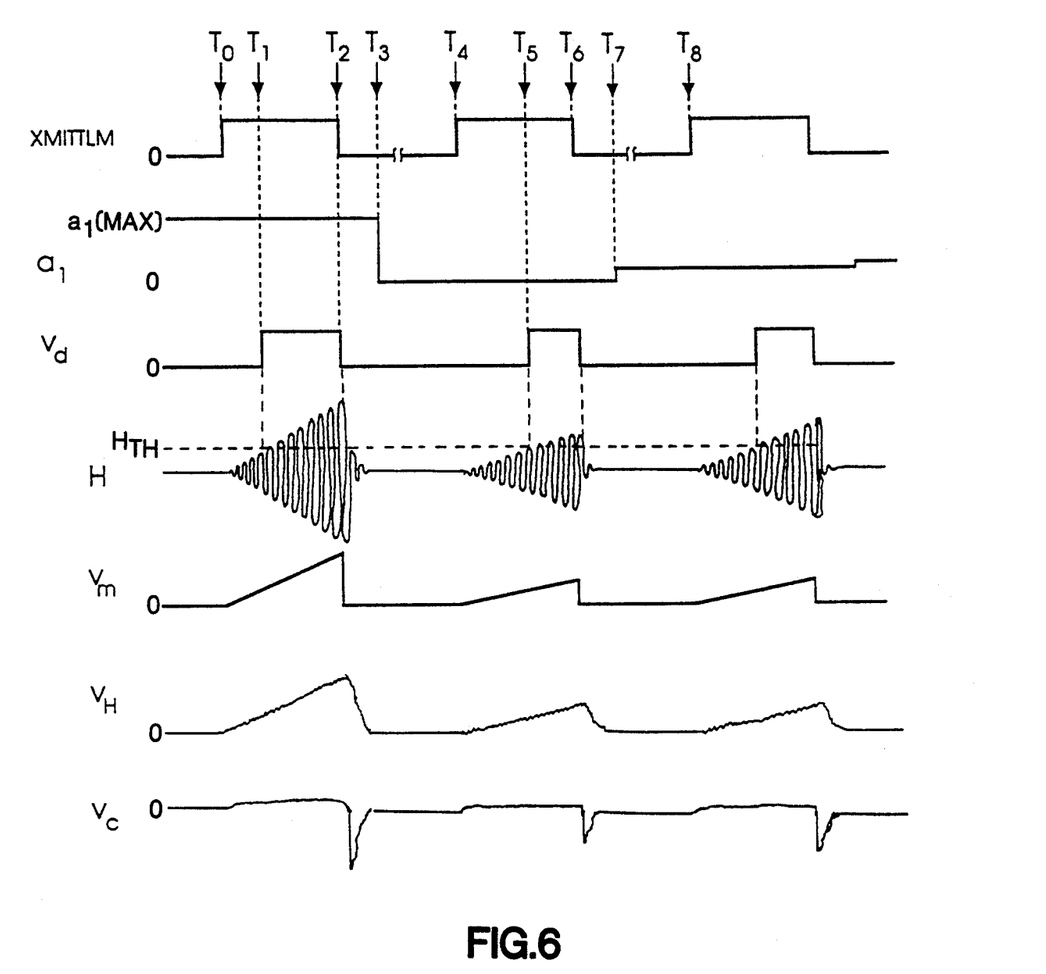
FIG. 6 is a timing diagram illustrating various signals present in the circuit represented by the block diagram of FIG. 2.

The manner in which the circuit of FIG. 2 operates to modulate the peak amplitudes of downlink RF bursts in response to the downlink signal strength may perhaps be more fully appreciated with reference to the timing diagram of FIG. 6. In FIG. 6, the various signals present in the circuit depicted in FIG. 2 are shown during the delivery of three consecutive downlink RF bursts. As shown in FIG. 6, delivery of telemetry pulses is initiated in response to square pulses in the XMITTLM signal. A first such pulse is initiated beginning at time $T_0$ in FIG. 6. Initially, the level of the $a_1$ signal representing the desired to downlink signal strength is assumed to be at its highest value $a_1(MAX)$, and the ramped output $v_m$ from envelope modulator 54 will have a correspondingly maximized peak amplitude, so that an RF burst of maximum peak amplitude will be delivered starting at time $T_0$. The signal $a_1$ being initially at its maximum value ensures that the first RF burst transmitted by programmer 12 will be as large as possible; as will be hereinafter described in greater detail, subsequent pulses may be reduced in amplitude, depending upon the strength of the downlink signal as detected in implantable device 10.

The RF signal transmitted by antenna 26 is shown as waveform H in FIG. 6. As previously described, downlink oscillator/driver 55 is responsive to the XMITTLM pulse beginning at time $T_0$, and to the modulation signal applied to its MODULATION input, to apply the 175-kHz linear ramping pulses shown in FIG. 6 to antenna 26, with the peak of each linear ramp burst being determined by the modulate signal $v_m$. Note from FIG. 6 that the RF burst detected in sense coil 32 and envelope detector 56 substantially corresponds in positive amplitude to the RF burst transmitted from antenna 26.

At time $T_2$, the first pulse in the XMITTLM pulse stream ends, causing downlink oscillator/driver 55 to discontinue the RF burst. In FIG. 6, the waveform $v_d$ represents the square pulse stream output from a downlink telemetry receiver (not shown) in IPG 16 of FIG. 2. Note that the rising edge of the first pulse in the $v_d$ pulse stream, at time T1 in FIG. 2, occurs some period of time after the corresponding rising edge in the XMITTLM pulse stream at time T0. This delay is due to the time required for the linear ramping RF bursts in the H waveform to rise to a level which exceeds the threshold $H_{TH}$ of the downlink telemetry receiver in IPG 16. As noted above, and in accordance with an important aspect of the present invention, the duration of the interval $T_x$ (beginning at time $T_1$ when the detected downlink signal first exceeds $H_{TH}$ of the downlink receiver, and ending with the trailing edge of the RF burst at time T2) provides an indication of the strength of the downlink signal as detected by antenna 18 in implanted device 10. This is because for stronger detected downlink signals, the ramping H waveform will exceed the implanted device receiver threshold $H_{TH}$ earlier than for weaker detected signals.

Timing circuitry (not shown) in IPG 16 is provided for measuring the interval $T_x$ (i.e., the time between $T_1$ and $T_2$) and for uplink telemetering a representation of this measured $T_x$ value to be received by antenna 26, and ultimately to be decoded by DL SS decoder 50. It is contemplated in the presently disclosed embodiment of the invention that the adjustments to the downlink envelope occur in conjunction with handshaking frames that are normally exchanged between implanted device 10 and programmer 12 to ensure continuous maintenance of the uplink and downlink channels which include the $T_x$ data needed for the purposes of the present invention. In this way, the integrity of the downlink channel can be frequently confirmed.

In the timing diagram of FIG. 6, implantable device 10 transmits the $T_x$ data (i.e., a value reflecting the time between $T_1$ and $T_2$) to programmer 12' at time $T_3$. The $T_x$ data is decoded by DL SS decoder 50. Since the $a_1$ signal was initially set to its maximum value $a_1(MAX)$, the $T_x$ interval for the first detected H burst was longer than necessary (i.e., the H burst was stronger than necessary). Accordingly, when the $T_x$ data from the first detected H burst is decoded at time $T_3$, DL SS decoder 50 reduces the $a_1$ signal to a lower level, as shown in FIG. 6.

With continued reference to FIGS. 2 and 6, a second XMITTLM square pulse is initiated by programmer control circuit 20 beginning at time $T_4$. Since the $a_1$ signal was reduced at time $T_3$, envelope modulator 54 issues an envelope signal $v_m$ starting at time $t_4$ that has a lower peak amplitude than the $v_m$ signal issued beginning at time $T_1$. As a result, a ramping H burst with a lower peak amplitude is transmitted, as shown in FIG. 6, beginning at time $T_4$. The H burst, as detected by implantable device 10, first exceeds the receiver threshold $H_{TH}$ at time $T_5$, and continues until time $T_6$.

At time $T_7$, implanted device 10 transmits $T_x$ data (i.e., a value reflecting the length of the interval between times $T_5$ and $T_6$) to programmer 12'. In this case, the $T_x$ interval was measured by implantable device 10 to be slightly shorter than desired. Accordingly, DL SS decoder is responsive to the $T_x$ data to raise the level of the $a_1$ signal slightly, at time $T_7$. This results in envelope modulator issuing a ramping signal $v_m$ having a slightly increased peak amplitude as compared with the previous one. This leads to the transmission, beginning at time $T_8$, of a ramping H burst having a peak amplitude slightly higher than that of the burst delivered beginning at time $T_4$.

From the foregoing discussion of the timing diagram of FIG. 6, those of ordinary skill in the art will appreciate that the system of FIG. 2 allows external programming unit 12' to be informed of the strength of downlink signals detected by implanted device 10. Since the downlink signal strength can be monitored for each RF burst in the downlink signal stream, the modulation of the downlink transmission amplitude by external unit 12' can occur on a continuous and ongoing basis, in order to take into account such variable factors as patient movement, detuning and internal loading problems in both implanted device 10 and external unit 12', and component aging and degradation in both implanted device 10 and external unit 12'.

In addition to being used by envelope modulator 54 to alter the peak amplitude of ramping downlink telemetry bursts, the $T_x$ data provided from implanted device 10' is also preferably used by programmer control circuit 20 to provide a telemetry status indication to the physician or clinician using external programmer 12'.

As noted above, it is well known in the prior art that programmer 12' is capable of monitoring uplink telemetry signal strength based upon the gain setting of uplink receiver 22. In accordance with one feature of the present invention, it is contemplated that a telemetry status indicator based upon both uplink and downlink signal strength can be provided. To this end, it is useful to express both uplink and downlink signal strength in terms of a signal strength value. For downlink signal strength $S_D$, this value can be obtained by taking the ratio of $a_1$ to $a_1(max)$, per FIG. 6; that is, $S_D$ may be defined according to the following expression:

$$S_D = \left(1 - \frac{a_1}{a_1(max)}\right)$$

where $0 \leq S_D \leq 1$. Similarly, those of ordinary skill in the art will appreciate that the uplink signal strength $S_U$ may be expressed as a value corresponding to the gain setting of uplink receiver, normalized such that like $S_D$, $S_U$ is a value within the range $0 \leq S_U \leq 1$.

Given $S_D$ and $S_U$, it is contemplated in accordance with the presently disclosed embodiment of the invention that an overall signal strength indicator S may be defined as the geometric mean of the uplink and downlink signal strength values $S_U$ and $S_D$; that is, an overall signal strength value S given by the following formula:

$$S = \sqrt{S_D \times S_U}$$

where $0 \leq S \leq 1$.

Provided with an indication of this S value, the physician or clinician would be able to optimize the programming head positioning on a dynamic basis.

Since telemetry detection margins for good signal-to-noise performance is more important for the relatively weaker uplink signal than for the downlink signal, a telemetry status indicator preferably provides some minimum margin away from downlink null borders. To this end, the overall strength indicator S can be weighted toward providing the desired downlink margin. That is, a modified or weighted downlink signal strength indicator value $S_D'$ may be defined and utilized in the computation of the overall signal strength indicator value, where $S_D'$ is related to the original downlink signal strength indicator $S_D$ by some non-linear function $W_D$.

Figure 7:
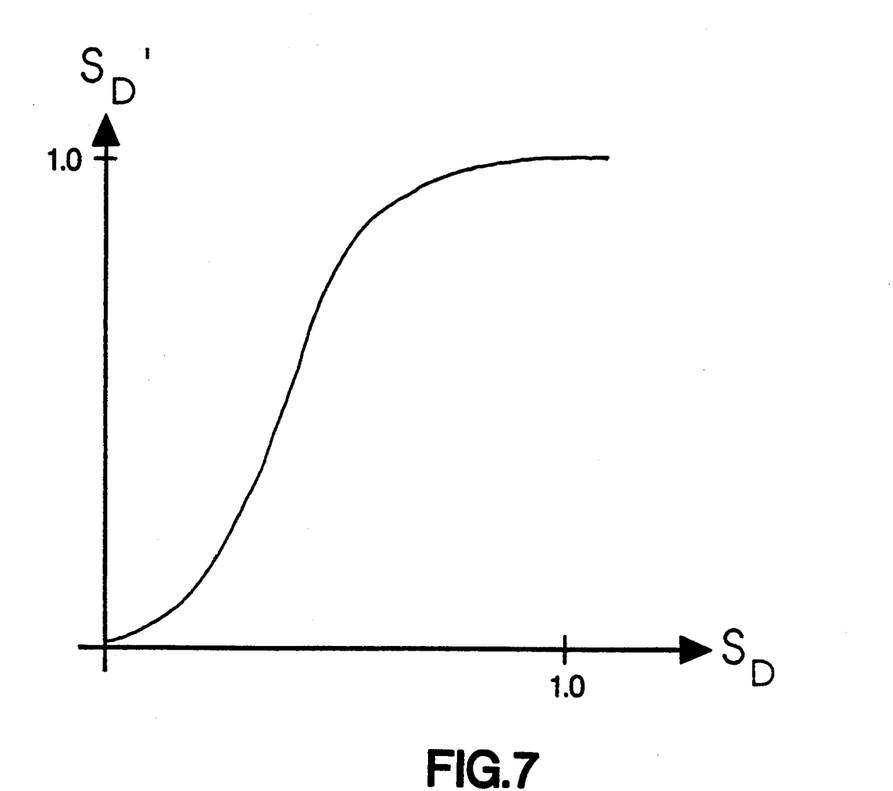
FIG. 7 is a graph illustrating a weighting function applied to the downlink signal strength indicator in accordance with one embodiment of the invention.

Referring to FIG. 7, there is shown a graph of $S_D$ versus $S_D'$ (where $S_D'$ is given by $W_D(S_D)$). Those of ordinary skill in the art will appreciate that the use of such a weighted downlink signal strength indicator value $S_D'$ to compute a weighted overall signal strength indicator S' (where S' is computed as the geometric mean of $S_U$ and $S_D'$ as for the unweighted indicator S) emphasizes the strength of the downlink signal as compared to the uplink signal.

Figure 8:
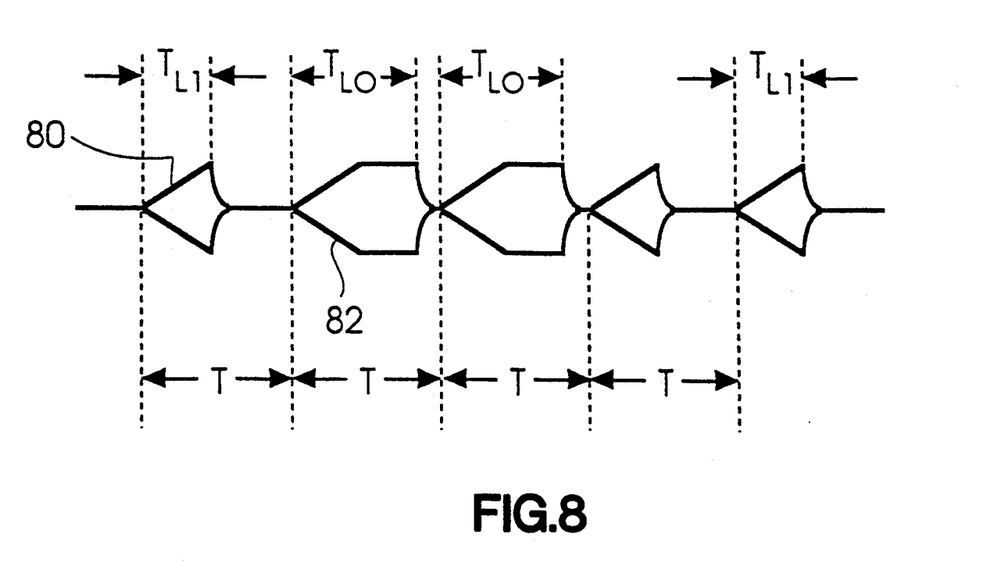
FIG. 8 is a diagram illustrating envelopes of downlink telemetry signals for a telemetry protocol in accordance with an alternative embodiment of the invention.

Since some form of pulse width measurement must be performed in implanted device 10 in order to ascertain the $T_x$ value, it is contemplated that such pulse width measurement capability may also be utilized for the purposes of measuring distinct pulse widths of downlink pulses. That is, instead of or in addition to pulse interval modulation for downlink telemetry, the pulse width measurement capability of the implanted device could allow a pulse width modulation scheme to be used for downlink telemetry. In FIG. 8, there is shown an illustrative diagram of a pulse width modulation telemetry scheme in accordance with an alternative embodiment of the invention. In FIG. 8, as with FIGS. 3 and 4 above, it is to be understood that an envelope for RF bursts is depicted, and that each burst is actually a 175-kHz RF signal having the shape or envelope shown.

The protocol represented in FIG. 8 is a synchronous modulation scheme, wherein a data bit (i.e., a "0" or a "1") is transmitted during each of a plurality of successive time slots of equal duration. This is to be contrasted with the asynchronous pulse interval modulation protocol previously described with reference to FIG. 4, in which the time required to transmit a "0" bit is longer than the time required to transmit a "1" bit.

In the protocol of FIG. 8, each time slot has a duration T, and a single RF burst is transmitted starting at the beginning of each time slot. A first burst, designated as 80 in FIG. 8, lasts for a time $T_{L1}$; burst 80 represents an encoded "1" in the pulse width modulation scheme. On the other hand, a second burst 82, transmitted in the next time slot in FIG. 8, lasts for a time interval $T_{L0}$, where $T_{L0}$ is greater than $T_{L1}$. Burst 82 represents an encoded "0" in the pulse width modulation scheme. It is contemplated that, for example, in systems operating at a 175-kHz carrier frequency, T could be on the order of 200-$\mu$Sec, while $T_{L0}$ is 150-$\mu$Sec and $T_{L1}$ is 100-$\mu$Sec.

As previously noted, the ability of pacemaker 10 to measure pulse widths for the purpose of obtaining the $T_x$ data in accordance with the above-described downlink signal strength determination allows pacemaker 10 to distinguish between the 100-$\mu$Sec and 150-$\mu$Sec bursts 80 and 82 in the pulse width modulation protocol of FIG. 8.

While the presently disclosed embodiment of the invention is believed to be particularly advantageous in the context of telemetry systems employing a dual-coil system as described in the above-referenced McQuilkin '532 patent, it is also believed that the present invention may be beneficially employed in the context of single-coil telemetry systems, wherein the uplink and downlink coupling maps are the same. Those of ordinary skill in the art will appreciate that in a single-coil system, the circuitry described hereinabove with reference to FIG. 2 could be simplified in that downlink signal strength decoder 50 would not be necessary.

Since the uplink and downlink telemetry coupling maps are the same in a single-coil system, the signal $a_1$ (see FIG. 6) used to control envelope modulator 54 could be generated directly by uplink receiver 22, and no downlink signal-strength decoder 50 would be required. In particular, the $a_1$ signal could be produced by the automatic gain control circuitry in uplink receiver 22, since the uplink signal strength, and hence also the downlink signal strength in a single-coil system, would be reflected in the gain setting of the uplink receiver.

From the foregoing detailed description of a specific embodiment of the invention, it should be apparent that a method and apparatus for assessing both uplink and downlink telemetry coupling for an implantable medical device has been disclosed. Although a particular embodiment of the invention has been described herein in some detail, it is to be understood that this has been done for the purposes of illustration only, and is not intended to be limiting with respect to the scope of the invention. It is contemplated that various alterations, substitutions, and/or modifications, including but not limited to those specifically discussed herein, may be made to the disclosed embodiment without departing from the spirit and scope of the present invention as defined in the appended claims, which follow.

What is claimed is:

1. An implantable medical device system including an implanted device and an external programming unit, said system comprising, in said external unit:
    a downlink radio-frequency (RF) transmitter adapted to transmit RF bursts each having a linear ramped envelope of predetermined duration and of predetermined peak amplitude;
    an uplink RF receiver adapted to receive digital information transmitted from said implanted device;

and in said implanted device:
    a downlink RF receiver adapted to detect said RF bursts transmitted by said external unit RF transmitter, and RF receiver having a detected signal threshold;
    a timing circuit, coupled to said downlink RF receiver and responsive to detection of one of said RF bursts by said downlink RF receiver to generate a digital downlink strength value reflecting the duration of a time interval during which said one detected RF burst exceeds said detected signal threshold;
    an uplink RF transmitter, coupled to said timing circuit and adapted to transmit said digital downlink strength value to said external unit.

2. An implantable medical device system in accordance with claim 1, further comprising, in said external unit:
    a processing circuit, coupled to said uplink RF receiver to receive said digital value transmitted from said uplink RF transmitter, said processing circuit responsive to receipt of said digital downlink strength value to issue a downlink signal strength signal;
    an envelope modulator circuit, coupled to said processing circuit and to said downlink RF transmitter, said envelope modulator circuit responsive to said downlink signal strength signal to vary said predetermined peak amplitude of said RF bursts transmitted from said downlink RF transmitter.

3. An implantable medical device system in accordance with claim 2, further comprising, in said external unit:
    a control circuit, coupled to said uplink RF receiver and responsive to said received digital downlink strength value exceeding a predetermined level to activate a telemetry status indicator.

4. An implantable medical device system in accordance with claim 3, wherein said telemetry status indicator comprises a light-emitting diode.

5. An implantable medical device system in accordance with claim 3, wherein said telemetry status indicator comprises an audible tone generator.

6. An implantable medical device system in accordance with claim 2, further comprising, in said external unit:
    an uplink signal monitoring circuit, coupled to said uplink RF receiver and responsive to detection of uplink signals by said uplink RF receiver to generate a digital uplink strength value reflecting uplink signal strength;
    a telemetry status circuit, coupled to said uplink signal monitoring circuit and to said uplink RF receiver, said telemetry status circuit responsive to receipt of said digital downlink strength value by said RF receiver and to generation of said digital uplink strength value to compute a telemetry status value.

7. An implantable medical device system in accordance with claim 6, wherein said telemetry status value is the geometric mean of said downlink strength value and said uplink strength value.

8. An implantable medical device system in accordance with claim 6, further comprising, in said external unit, a telemetry status indicator circuit, coupled to said telemetry status circuit and responsive to said telemetry status value exceeding a predetermined minimum to activate a telemetry status indicator.

9. An implantable medical device system in accordance with claim 8, wherein said telemetry status indicator is a light-emitting diode.

10. An implantable medical device system in accordance with claim 8, wherein said telemetry status indicator is an audible tone generator.

11. A method of controlling the strength, as received, of telemetry signals transmitted in the form of RF bursts from an RF transmitter to an RF receiver having a detected signal threshold, comprising the steps of:
    (a) defining a duration and peak amplitude of a linear-ramping envelope for said RF bursts transmitted from said transmitter;
    (b) transmitting, from said RF transmitter, an RF burst having said envelope from step (1);
    (c) detecting, in said RF receiver, said RF burst transmitted in step (b);
    (d) timing an interval during which said RF burst detected in step (c) exceeds said RF receiver's detected signal threshold, to obtain a time value;
    (e) communicating said time value obtained in step (d) to said RF transmitter;
    (f) redefining said envelope peak amplitude in inverse proportion to said time value.

12. The method of claim 11, further comprising the step of:
    (g) providing a telemetry status indication when said time value exceeds a predetermined minimum.

* * * * *